(12) United States Patent
Brooks et al.

(10) Patent No.: US 6,346,116 B1
(45) Date of Patent: Feb. 12, 2002

(54) DISTAL PROTECTION DEVICE

(75) Inventors: Dennis L. Brooks, Windsor; Robert D. Lashinski, Sebastopol, both of CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 0 days.

(21) Appl. No.: 09/366,391

(22) Filed: Aug. 3, 1999

(51) Int. Cl.⁷ .......................... A61M 29/00; A61B 17/22
(52) U.S. Cl. ........................ 606/200; 606/159
(58) Field of Search .................. 606/200, 194, 606/191, 108, 159, 198; 604/96, 104–106, 22

(56) References Cited

U.S. PATENT DOCUMENTS

| | | |
|---|---|---|
| 4,425,908 A | 1/1984 | Simon |
| 4,723,549 A | 2/1988 | Wholey et al. |
| 4,790,812 A | 12/1988 | Hawkins, Jr et al. |
| 4,873,978 A | 10/1989 | Ginsburg |
| 4,926,858 A | 5/1990 | Gifford, III et al. |
| 5,071,407 A | 12/1991 | Termin et al. |
| 5,108,419 A | 4/1992 | Reger et al. |
| 5,160,342 A | 11/1992 | Reger et al. |
| 5,329,942 A | 7/1994 | Gunther et al. |
| 5,421,832 A | 6/1995 | Lefebvre |
| 5,549,626 A | 8/1996 | Miller et al. |
| 5,695,519 A | 12/1997 | Summers et al. |
| 5,814,064 A | 9/1998 | Daniel et al. |
| 5,827,324 A | 10/1998 | Cassell et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A * | 8/1999 | Patterson et al. ........... 604/508 |
| 5,972,019 A | 10/1999 | Engelson et al. |
| 6,027,520 A | 2/2000 | Tsugita et al. |
| 6,042,598 A | 3/2000 | Tsugita et al. |
| 6,059,814 A | 5/2000 | Ladd |
| 6,066,149 A | 5/2000 | Samson et al. |
| 6,066,158 A * | 5/2000 | Engelson et al. ........... 606/200 |
| 6,096,053 A | 8/2000 | Bates |
| 6,123,715 A | 9/2000 | Amplatz |
| 6,142,987 A | 11/2000 | Tsugita |
| 6,152,946 A | 11/2000 | Broome et al. |
| 6,165,200 A | 12/2000 | Tsugita et al. |
| 6,171,327 B1 | 1/2001 | Daniel et al. |
| 6,179,859 B1 | 1/2001 | Bates et al. |

FOREIGN PATENT DOCUMENTS

| | | |
|---|---|---|
| FR | 2 768 326 | 3/1999 |
| WO | WO 96/01591 | 1/1996 |
| WO | WO 98/33443 | 8/1998 |
| WO | WO 99/22673 A1 | 5/1999 |
| WO | WO 99/23976 | 5/1999 |
| WO | WO 99/44510 A1 | 6/1999 |
| WO | WO 00/16705 A1 | 3/2000 |

* cited by examiner

Primary Examiner—Olik Chaudhuri
Assistant Examiner—Hoa B. Trinh
(74) Attorney, Agent, or Firm—Catherine C. Makesh

(57) ABSTRACT

The present invention is a distal protection device for use with a delivery member. A filter assembly is located on the distal end of the delivery member. The filter is deployed distally of the region to be treated to capture emboli released during and immediately after the procedure. The filter is then retracted to retain any captured emboli and then removed from the patient.

19 Claims, 5 Drawing Sheets

DISTAL PROTECTION DEVICE

FIELD OF THE INVENTION

The present invention relates generally to endovascular devices for capturing particulate. More particularly, the invention relates to a filter assembly located at the distal end of a delivery member to capture emboli in a blood vessel during a vascular procedure and then removing the captured emboli from the patient after completion of the procedure.

BACKGROUND OF THE INVENTION

A variety of treatments exist for compressing or removing athersclerotic plaque in blood vessels. The use of an angioplasty balloon catheter is common in the art as a minimally invasive treatment to enlarge a stenotic or diseased blood vessel. This treatment is known as percutaneous transluminal angioplasty, or PTA. To provide radial support to the treated vessel in order to prolong the positive effects of PTA, a stent may be implanted in conjunction with the procedure.

Removal of the entire thrombosis or a portion of the thrombosis sufficient enough to enlarge the stenotic or diseased blood vessel may be accomplished instead of a PTA procedure. Thrombectomy and atherectomy are well known minimally invasive procedures that mechanically cut or abrade the stenosis within the diseased portion of the vessel. Alternatively, ablation therapies use laser or RF signals to superheat or vaporize the thrombis within the vessel. Emboli loosened during such procedures are removed from the patient through the catheter.

During each of these procedures, there is a risk that emboli dislodged by the procedure will migrate through the circulatory system and cause clots and strokes. Thus, practitioners have approached prevention of escaped emboli through use of occlusion devices, filters, lysing and aspiration techniques. In atherectomy procedures, it is common to remove the cut or abraded material by suction though an aspiration lumen in the catheter or by capturing emboli in a filter or occlusion device positioned distal of the treatment area.

Prior art filters or occlusion devices are associated with either a catheter or guidewire and are positioned distal of the area to be treated. One prior art collapsible filter device includes a filter deployed by a balloon distal of a dilatation balloon on the distal end of a catheter. The filter consists of a filter material secured to resilient ribs. The ribs are mounted at the distal end of the catheter. A filter balloon is located between the catheter exterior and the ribs. Inflation of the filter balloon extends the ribs outward across the vessel to form a trap for fragments loosened by a dilatation balloon. When the filter balloon is deflated, the resilient ribs retract against the catheter to retain the fragments during withdrawal of the catheter.

Another prior art filter arrangement includes several filter elements fastened in spaced apart arrangement along the length of a flexible elongate member. This forms an open-mouthed tubular sock like arrangement to capture the emboli within. The filter is collapsed around the flexible elongate member by wrapping it spirally.

Yet another prior art filter includes a filter mounted on the distal portion of a hollow guidewire or tube. A core wire is used to open and close the filter. The filter has an expandable rim at its proximal end formed by the core wire. The filter is secured at the distal end to the guide wire.

Another prior art device has a filter made from a shape memory material. The device is deployed by moving the proximal end of the filter towards the distal end. It is collapsed and withdrawn by moving a sheath over the filter and then removing the sheath and filter.

A further prior art filter device discloses a compressible polymeric foam filter mounted on a shaft that is inserted over the guidewire. The filter is inserted collapsed within a housing which is removed to deploy the filter once in position. The filter is retracted by inserting a large bore catheter over the shaft and the filter and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be inserted onto the shaft and the filter is withdrawn into the shaft for removal from the patient.

Other known prior art filters are secured to the distal end of a guidewire with a tubular shaft. Stoppers are placed on the guidewire proximal and distal of the filter, allowing the filter to move axially and retract independent of the guidewire. A sheath is used to deploy and compress the filter.

One problem associated with known filter arrangements is that emboli may not be fully contained within the filter. Emboli can build up in the area just proximal of the filter, including any frame portion of the filter assembly. As the filter is closed, emboli not fully contained in the filter can escape around the filter into the circulatory system and cause potentially life threatening strokes. While the blood flow is inhibited when an occlusion device is used during the procedure, emboli can escape as the occlusion device is withdrawn from the treatment area.

Therefore, what is needed is a filter arrangement that addresses the problem of emboli not fully contained in the filter assembly or captured by an occlusion device. Furthermore, there is a need for a filter assembly that is adaptable for delivery with standard PTCA balloon or stent delivery catheters. Additionally there is a need for a filter arrangement that is secure by being mounted at its distal and proximal ends to the delivery member ensuring proper placement of the filter throughout deployment, capture of the emboli and subsequent removal of the filter and captured emboli.

SUMMARY OF THE INVENTION

The present invention is a distal protection device for use in vascular procedures. The distal protection device includes a filter assembly adjacent the distal end of a delivery member used in the procedure. The proximal and distal ends of the filter assembly are fixed to the delivery member such that the ends cannot move longitudinally along the delivery member, but may rotate independent of the delivery member core. The filter assembly includes an expandable frame with a distal portion acting as the emboli filter. The emboli filter is sized sufficiently to expand and cover the cross sectional area of the vessel just distal of the intended treatment area.

The filter assembly may have a variety of configurations. In one embodiment, the frame consists only of the proximal portion of the filter assembly, with the distal half formed from filter material. The frame can have a braided configuration or consist of a sinusoidal ring element adjacent the filter material with helical segments extending from the sinusoidal ring to the delivery member. In another embodiment, the frame forms a basket arrangement and includes the filter material in the distal half of the basket. Such a frame can be configured with a tighter braid on the distal end, thus obviating the need for a filter material.

The filter assembly further includes a moveable sheath for positioning the emboli filter between an expanded position and a collapsed position. The sheath extends over the frame, collapsing the frame and filter of the assembly as they are drawn into the sheath. Likewise, when the frame and filter are removed from the sheath, they will expand so the filter will cover the cross sectional area of the vessel distal of the treatment area.

Alternative embodiments of the filter assembly can include an aspiration lumen extending through the sheath or a flushing lumen extending through the sheath. This allows large emboli to be lysed or aspirated prior to retracting the filter and removing it from the patient.

The sheath is configured to be used with either a rapid exchange arrangement or an over the wire arrangement as well known to those skilled in the art.

BRIEF DESCRIPTION OF DRAWINGS

For a more complete understanding of the features, aspects, and advantages of the present invention, reference is now made to the following description, appended claims, and accompanying drawings wherein:

DETAILED DESCRIPTION OF THE PREFERRED EMBODIMENTS

Figure 1:
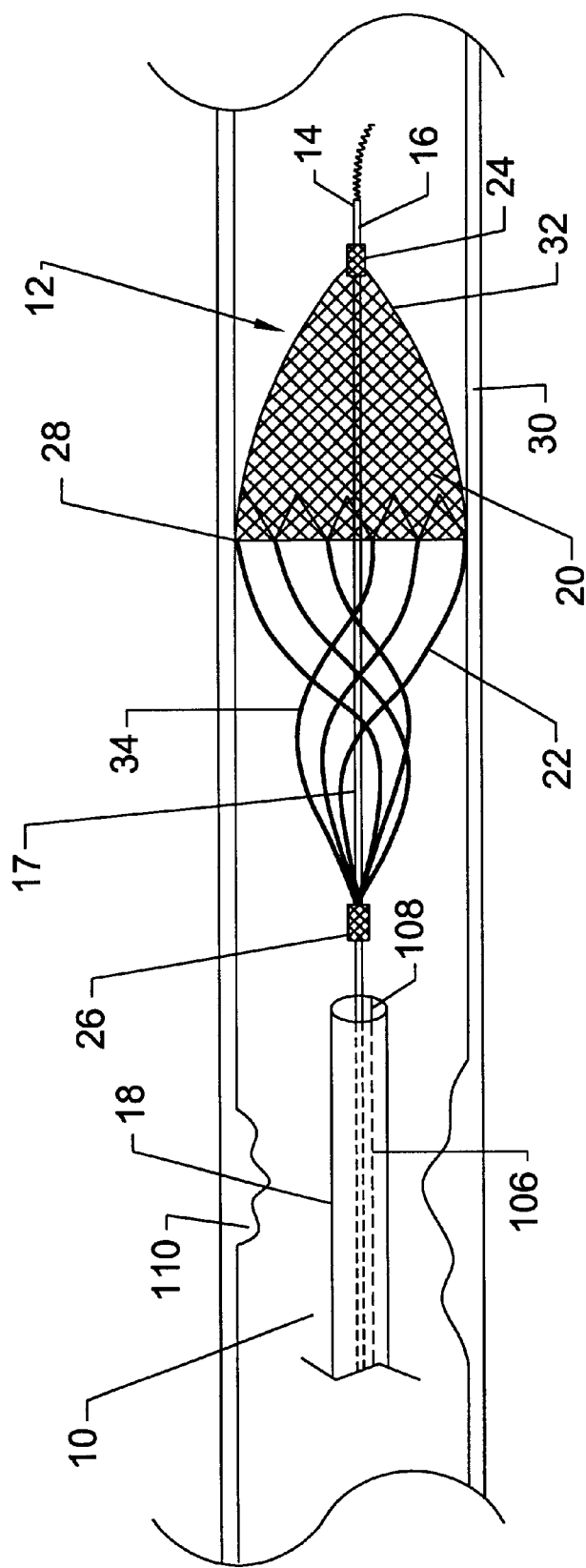
FIG. 1 is a side view of a sheath and delivery member incorporating a distal protection device of the present invention, with the distal protection device shown deployed in a vessel.
Figure 2:
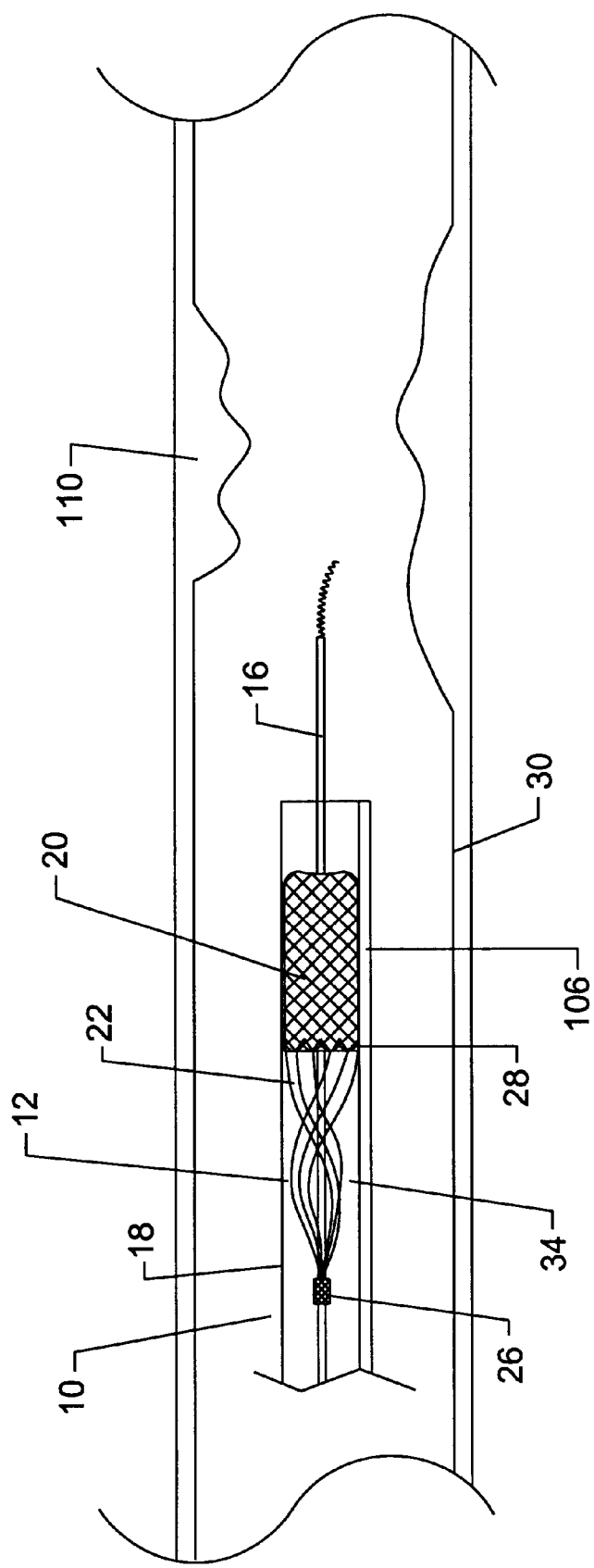
FIG. 2 is a cross section view taken of the distal portion of a sheath and delivery member incorporating a distal protection device of the present invention, with the distal protection device shown constrained in the sheath.

The present invention is a distal protection device, designated 10 in FIG. 1 for use in minimally invasive procedures, such as vascular procedures or other procedures where the practitioner desires to capture material that may be dislodged during the procedure. The distal protection device 10 includes a filter assembly 12 located adjacent the distal end 14 of a delivery member 16. In this preferred embodiment delivery member 16 can be a modified guidewire assembly, hereinafter referred to as either "delivery member" or "guidewire". Filter assembly 12 is delivered, deployed and retrieved by a sheath 18 arranged to be slid over filter assembly 12. When the distal protection device 10 is in a constrained position, filter assembly 12 is collapsed within sheath 18 as shown in FIG. 2. When filter assembly 12 is deployed, sheath 18 is withdrawn releasing filter assembly 12 as shown in FIG. 1.

Filter assembly 12 includes a filter 20 and a frame 22 and is secured to guidewire 16 at its filter assembly distal end 24 and filter assembly proximal end 26. Preferably, the filter assembly ends 24 and 26 are fixed in the longitudinal position, but are capable of rotational movement independent of the guidewire core 17 while maintaining the longitudinal position. Filter 20 is formed from a suitable mesh or porous material that will filter emboli from blood while permitting sufficient perfusion therethrough. For example, a porous filter can be formed from urethane material by adding salt, sugar or other granular particles during the casting of the urethane filter. Following the cutting and curing processes, these granular particles are dissolved forming a porous urethane filter as well known to those skilled in the art. Other suitable filter materials may include nylon, ePTFE, teflon, kevlar and the like having an appropriate porous construction to filter emboli from blood passing through the filter.

Filter assembly 12 is positioned concentric with guidewire 16. Filter 20 is sized such that when it is fully deployed, as in FIG. 1, its proximal edge 28 will contact the inner surface of the blood vessel wall 30. The inner surface contact is preferably maintained over the entire cross section to prevent any emboli from escaping past filter 20. Filter 20 is preferably secured at its proximal edge 28 to frame 22 and at its distal portion 32 to the guidewire 16.

Frame 22 of filter assembly 12 is an expandable frame made from a shape memory material, such as nitinol, a suitable polymer, stainless steel or other suitable materials. Several struts, designated generally as 34, extend from the guidewire 16 at filter asembly proximal end 26 to proximal edge 28 of filter 20, to form frame 22, as seen in FIGS. 1 and 2.

Figure 3:
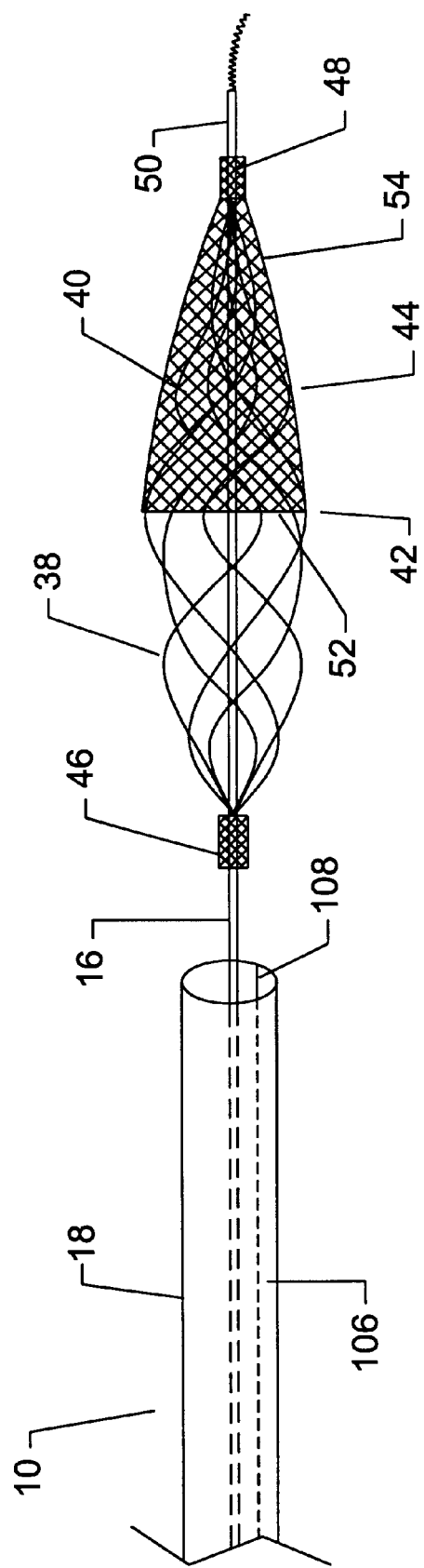
FIG. 3 is a side view of a second filter arrangement of the present invention shown deployed.

Alternatively, struts 38 may extend around filter 40 forming a basket frame 42 with filter 40 on at least the distal portion 44 of basket frame 42 as shown in FIG. 3. In such an arrangement, basket frame 42 is secured preferably at its proximal end 46 and distal end 48 to guidewire 50. As with the embodiment of FIG. 1, basket frame 42 is fixed on the guidewire at a longitudinal position where it is capable of rotational movement independent of guidewire 50. Filter 40 is secured at its proximal end 52 to basket frame 42 and at its distal end 54 to basket frame 42. Filter 40 can be secured to the struts 38 on the distal portion 44 of basket frame 42. Alternatively, filter 40 may be formed on basket frame 42 by dip coating select portions of basket frame 42 with a suitable material such as urethane and treating the material to form the desired porous structure on distal portion 44.

Figure 4:
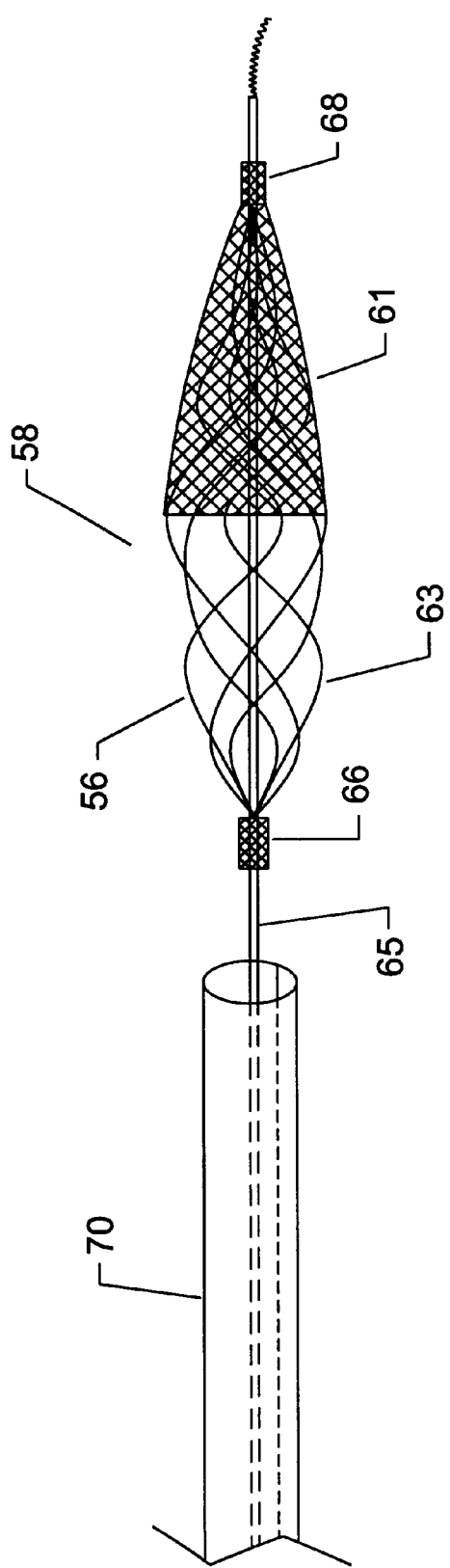
FIG. 4 is a side view of a third filter arrangement of the present invention shown deployed.

A variety of strut configurations are suitable such as the braid configuration shown in FIG. 1. Struts 56 of filter assembly basket 58 shown in FIG. 4 have a dense braid on distal portion 60 that transitions to a less dense braid on proximal portion 62. Filter material may be located on distal portion 60 by either having a separate filter material or by dip coating selected portions of the basket 58 as discussed above with respect to the embodiment shown in FIG. 3. Alternatively, the braid of the struts 56 may be sufficiently dense on distal portion 60 to act as a porous filter thus obviating the need for a separate filter material or selective dip coating of basket 58. Filter assembly basket 58 is fixed to the guidewire 64 at its proximal end 66 and distal end 68. Again, filter assembly basket 58 is preferably fixed at a longitudinal position on guidewire 64 where it is capable of rotational movement independent of the guidewire core. A sheath 70 is used to deploy filter assembly basket 58.

Figure 5:
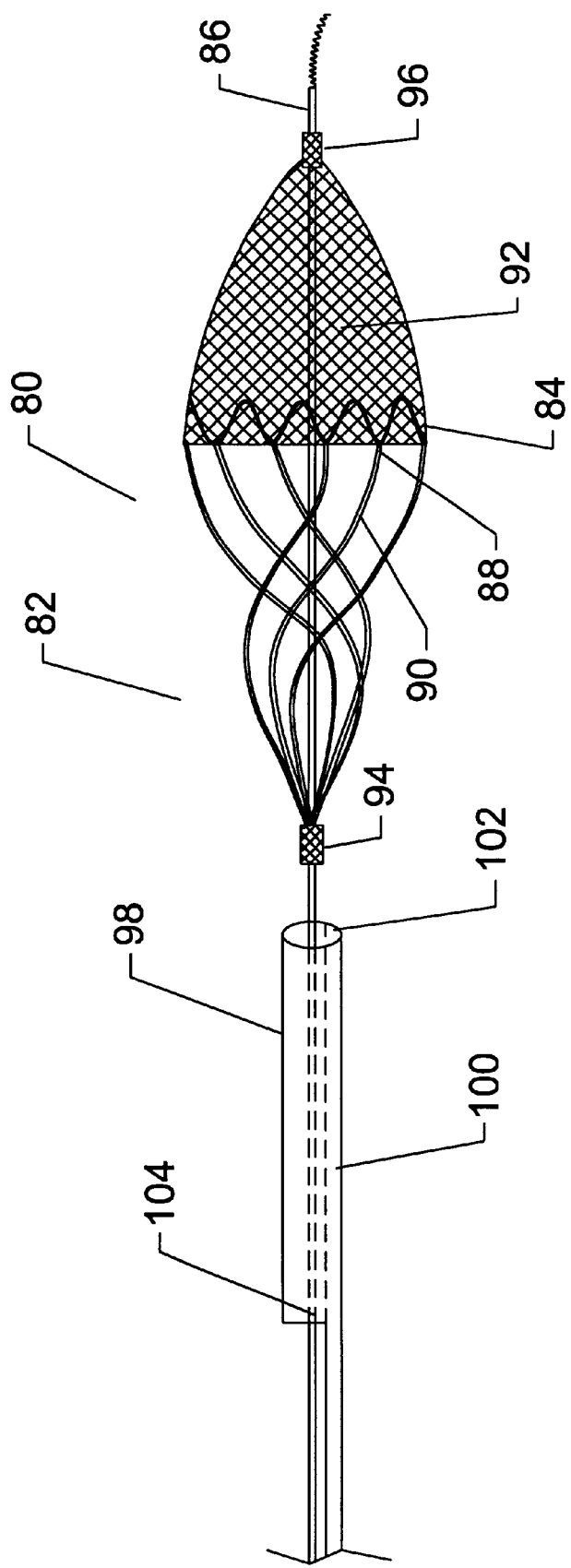
FIG. 5 is a side view of a rapid exchange styled delivery sheath and a fourth filter arrangement of the present invention.

Filter assembly 80 shown in FIG. 5 is similar to the filter arrangement of FIG. 1. Frame 82 consists of a distal ring 84 formed from a sinusoidal element. Extending from ring 84 to the guide wire 86 are helical members. For example, one such helical member 90 extends between apex 88 of ring 84 and guidewire 86. Distal end 96 of filter 92 is secured to guidewire 86.

Sheath 98 includes an aspiration lumen 100 and lysing lumen 102. While two lumens are shown, as known to those skilled in the art, only an aspiration or lysing lumen may be incorporated in sheath 98. Sheath 98 also includes a short guidewire lumen 104 resulting in a sheath configured as a rapid exchange sheath.

The deployment of the filter assembly will now be described. The deployment mechanism includes sheath 18 that is sized to travel over guidewire 16 and receive filter assembly 2 therein as shown in FIG. 2. Sheath 18 may incorporate an aspiration lumen 160. Additionally, sheath 18 may incorporate a flushing lumen 108 (FIG. 1) to enable the practitioner to flush the filter assembly with a lysing agent prior to and during the procedure to remove emboli lodged on the struts.

Sheath 18, 98 is constructed for use as either an over the wire system as shown in FIG. 1 or a rapid exchange system as seen in FIG. 5.

In operation, sheath 18 is extended over guidewire 16 until it fully covers filter assembly 12 as shown in FIG. 2. Sheath 18, filter assembly 12 and guidewire 16 are then inserted into the patient and routed to the area to be treated designated as 110 in FIG. 1. Filter assembly 12 and sheath 18 are positioned past the area 110 to be treated. Sheath 18 is then withdrawn, releasing struts 34 of filter assembly 12. As struts 34 resume their unrestrained position, filter 20 expands to fill the cross sectional area of the vessel. Sheath 18 may then be completely withdrawn from delivery member 16 and then an appropriate second delivery member, such as a treatment catheter, is routed over guidewire 16 to the treatment area.

During and after the treatment such as, an angioplasty, atherectomy or the like procedure, emboli can be dislodged. The emboli will travel downstream and be captured by filter 20. The treatment catheter is removed after the procedure and sheath 18 is loaded on guidewire 16 and delivered to the treatment area 110. Prior to collapsing the filter assembly 12, the practitioner can aspirate the area to remove any loose emboli that may not be sufficiently captured in filter 20. For example, emboli may be lodged on struts 34 proximal of filter 20. When filter 20 is collapsed, these emboli may escape into the blood stream. Thus, the particles should be removed. Furthermore, the practitioner may choose to flush the area with a lysing agent to reduce the size of the emboli within filter 20 or struts 34 prior to recapturing the filter.

The practitioner then extends sheath 18 over filter assembly 12 compressing filter 20 and the captured emboli within sheath 18. Sheath 18, filter assembly 12 and guidewire 16 can then be removed from the patient.

The foregoing embodiments and examples are illustrative and are in no way intended to limit the scope of the claims set forth herein. For example, the filter material can be a nylon or PET that has holes poked therethrough. The filter can be mounted onto a delivery member such as a catheter or integral with a dilatation balloon for advancing across a tight stenosis. These and other alternatives are within the scope of the invention.

We claim:

1. A distal protection device for capturing emboli during an endovascular procedure at a treatment area, said device comprising:
    a delivery member having a proximal end and a distal end;
    a self-expanding filter assembly adjacent said distal end of said delivery member, said filter assembly having a proximal portion and a distal portion, and having a proximal end longitudinally fixed to said delivery member and a distal end longitudinally fixed to said delivery member; and
    a sheath being moveable over at least part of the proximal portion of said filter assembly for positioning said filter assembly between a deployed position and a collapsed position.

2. The distal protection device of claim 1 wherein said filter assembly distal portion comprises a filter material and is sized to fill a selected cross-sectional area distal of the treatment area.

3. The distal protection device of claim 1 wherein said filter assembly proximal portion comprises an expandable frame.

4. The distal protection device of claim 3 wherein said expandable frame has a braid configuration.

5. The distal protection device of claim 3 wherein said expandable frame includes a sinusoidal ring at its distal end.

6. The distal protection device of claim 1 wherein said filter assembly comprises an expandable basket.

7. The distal protection device of claim 6 wherein said expandable basket comprises a braid structure that transitions from a dense weave at said filter assembly distal portion to a less dense weave at said filter assembly proximal portion.

8. The distal protection device of claim 6 wherein said basket further includes a proximal portion and a distal portion and a filter material positioned at the distal portion, said filter material being sized sufficiently to expand and cover a cross-sectional area distal of the treatment area.

9. The distal protection device of claim 1 wherein said sheath is concentric with said delivery member.

10. The distal protection device of claim 1 wherein said filter assembly is concentric with said delivery member.

11. The distal protection device of claim 1 wherein said filter assembly comprises an expandable frame forming said proximal portion thereof and an expandable porous filter comprising said distal portion thereof.

12. The distal protection device of claim 1 wherein said sheath includes an aspiration lumen.

13. The distal protection device of claim 1 wherein said sheath includes a flushing lumen.

14. A method of using a distal protection device in a vascular treatment region within a patient, said method comprising:
    providing a delivery member and a moveable sheath covering a self-expanding filter assembly located adjacent a distal end of said delivery member, said delivery member being longitudinally fixed to said filter assembly at a proximal end and a distal end of said filter assembly;
    positioning said filter assembly distal of said treatment region;
    retracting said sheath proximally to deploy said filter assembly distal of the treatment region;
    conducting a procedure at said treatment region;
    capturing emboli in said filter assembly during said procedure;
    moving said sheath distally over said filter assembly to at least partially collapse said filter around said captured emboli; and
    removing said at least partially collapsed filter and captured emboli from said patient.

15. A method of claim 14 and further including advancing a second delivery member over said first delivery member.

16. A method of claim 15 and further including performing a procedure at said treatment region with said second delivery member.

17. A method of claim 14 wherein said filter assembly includes a filtering material and the step of retracting said sheath to deploy said filter assembly also comprises expanding said filtering material of said filter assembly.

18. A method of claim 14 and further comprising aspirating captured emboli from said filter assembly prior to collapsing said filter.

19. A method of claim 14 and further comprising flushing said filter assembly with a lysing agent prior to collapsing said filter.

* * * * *